United States Patent [19]
Schneider et al.

[11] Patent Number: 6,030,628
[45] Date of Patent: *Feb. 29, 2000

[54] COSMETIC OR DERMATOLOGICAL PREPARATIONS CONTAINING GLYCOGLYCEROLIPIDS AND THEIR USE AS SURFACTANTS

[75] Inventors: Günther Schneider; Oliver Scheel; Joachim Thiem, all of Hamburg, Germany

[73] Assignee: Beiersdorf AG, Hamburg, Germany

[ * ] Notice: This patent is subject to a terminal disclaimer.

[21] Appl. No.: 08/914,930

[22] Filed: Aug. 20, 1997

[30] Foreign Application Priority Data

Aug. 23, 1996 [DE] Germany .............. 196 34 020

[51] Int. Cl.$^7$ .............. A61K 7/42; A61K 31/70; A61K 7/00; C07H 3/00
[52] U.S. Cl. .............. 424/401; 514/25; 514/53; 514/62; 536/4.1
[58] Field of Search .............. 424/401; 514/25, 514/53, 62; 536/4.1

[56] References Cited

U.S. PATENT DOCUMENTS 5,891,854  4/1999  Thiem et al. .

FOREIGN PATENT DOCUMENTS 62-224140  6/1989  Japan .
9-38478    2/1997  Japan .
94/06408   3/1994  WIPO .

OTHER PUBLICATIONS

Noevir, *World Patents Index*, #96–006866, Jan. 8, 1996.

*Primary Examiner*—Thurman K. Page
*Assistant Examiner*—Brian K. Seidleck
*Attorney, Agent, or Firm*—Sprung Kramer Schaefer & Briscoe

[57] ABSTRACT

Cosmetic or pharmaceutical preparations, characterized by an effective content of pharmaceutically and/or cosmetically acceptable glycoglycerolipids.

16 Claims, No Drawings

COSMETIC OR DERMATOLOGICAL PREPARATIONS CONTAINING GLYCOGLYCEROLIPIDS AND THEIR USE AS SURFACTANTS

The present invention relates to novel processes for the preparation of glycoglycerolipids and to their use in the field of cosmetic and pharmaceutical dermatology. The present invention relates in particular to active substances and to cosmetic or dermatological preparations containing combinations of such active substances. The present invention relates especially to active substances which have surfactant properties and/or which increase the moisture content of the skin. The invention further relates to cosmetic and dermatological preparations containing such substances. In one preferred embodiment the present invention relates to cosmetic cleansers. In another embodiment the present invention relates to cosmetic preparations containing substances which increase the moisture content of the skin.

The outermost layer of the epidermis, the stratum corneum (horny layer), is of particular significance as an important barrier layer, inter alia for protection from environmental influences and drying. The horny layer is constantly being worn away in contact with the environment and must therefore be continually renewed.

A skin model widely used by modern experts treats the stratum corneum as a two-component system similar to a brick wall (bricks-and-mortar model). In this model the corneocytes (horny cells) correspond to the bricks and the lipid membrane of complicated composition in the intercellular spaces corresponds to the mortar.

Apart from their barrier action against external chemical and physical influences, the epidermal lipids also contribute to the cohesive strength of the horny layer and affect the smoothness of the skin. In contrast to the sebaceous lipids, which do not form a closed film on the skin, the epidermal lipids are distributed over the whole of the horny layer.

The extremely complex interaction between the moisture binding substances and the lipids of the upper layers of the skin is very important for the regulation of the moisture content of the skin. This is why cosmetics normally contain water binding substances in addition to balanced lipid mixtures and water.

However, not only the chemical composition but also the physical behaviour of these substances is important. It is therefore desirable to develop emulsifiers or surfactants of very good biocompatibility and with liquid crystalline properties. Products formulated therewith support the liquid crystalline organization of the intercellular lipids of the stratum corneum, thereby improving the barrier properties of the horny layer. It is particularly advantageous if their molecular components consist of substances which occur naturally in the epidermis.

It was surprising, and could not be anticipated by those skilled in the art, that cosmetic or pharmaceutical preparations characterized by an effective content of one or more pharmaceutically and/or cosmetically acceptable glycoglycerolipids remedy the disadvantages of the state of the art.

Advantageously, in terms of the present invention, the glycoglycerolipid or glycoglycerolipids are selected from the group of substances of the structure

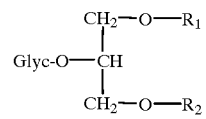

in which Glyc is a monosaccharide residue coupled to the glyceryl radical via an α- or β-glycosidic linkage, especially a pentosyl residue or hexosyl residue, it being possible for a hexosyl residue to be either in the furanosyl form or in the pyranosyl form, in which the monosaccharide residue may also be a deoxy sugar residue or an amino sugar residue (a particularly advantageous example being the 2-acetamido-2-deoxy-D-glucopyranoside residue, which is derived from chitin), and in which $R_1$ and $R_2$ independently of one another are selected from the group comprising H and saturated or unsaturated, branched or unbranched acyl having 1–24 carbon atoms, although at least one of the radicals $R_1$ and $R_2$ is an acyl radical.

However, it may also be advantageous to select the glycoglycerolipid or glycoglycerolipids from the group of substances of the structure

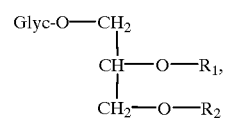

in which Glyc is a monosaccharide residue coupled to the glyceryl radical via an α- or β-glycosidic linkage, especially a pentosyl residue or hexosyl residue, it being possible for a hexosyl residue to be either in the furanosyl form or in the tyranosyl form, in which the monosaccharide residue may also be a deoxy sugar residue or an amino sugar residue (a particularly advantageous example being the 2-acetamido-2-deoxy-D-glucopyranoside residue, which is derived from chitin), and in which $R_1$ and $R_2$ independently of one another are selected from the group comprising H and saturated or unsaturated, branched or unbranched acyl having 1–24 carbon atoms, although at least one of the radicals $R_1$ and $R_2$ is an acyl radical.

The hexoses on which the hexosylglycerolipids according to the invention are based are preferably selected from the group comprising aldohexoses, usually in their pyranoid form, i.e. allo(pyrano)se, altro(pyrano)se, gluco(pyrano)se, manno(pyrano)se, gulo(pyrano)se, ido(pyrano)se, galacto(pyrano)se and talo(pyrano)se. It is also advantageous to select the hexoses from the group comprising amino sugars.

The use of D-hexosylglycerolipids is advantageous; nevertheless, it may also be advantageous, in terms of the present invention, to use L-hexosylglycerolipids.

It may also be advantageous, in terms of the present invention, to use hexosylglycerolipids based on D- or L-ketohexoses, i.e. psicose, fructose, sorbose or tagatose, usually present in their furanoid form.

It is particularly advantageous in terms of the present invention to select the glycoglycerolipid or glycoglycerolipids from the group of substances of the structure

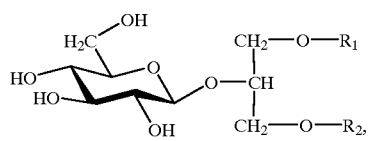

in which $R_1$ and $R_2$ independently of one another are selected from the group comprising H and saturated or unsaturated, branched or unbranched acyl having 1–24 carbon atoms. $R_1$ and $R_2$ are preferably identical. $R_1$ and/or $R_2$ are particularly preferably selected from the group comprising octanoyl, decanoyl, dodecanoyl, tetradecanoyl, hexadecanoyl, octadecanoyl and eicosanyl.

Particularly preferred hexosylglycerides are 1,3-diacyl derivatives of 2-O-(β-D-glucopyranosyl)-sn-glycerol. However, it can also be advantageous in terms of the present invention to use 1-monoacyl derivatives of 2-O-(β-D-glucopyranosyl)-sn-glycerol.

It could not therefore have been predicted by those skilled in the art that the glycoglycerolipids according to the invention or cosmetic or dermatological preparations containing them would have a better moisturizing action, would have a better action against skin ageing, would be more suitable surfactants and would be distinguished by a better biocompatibility than the active substances, active substance combinations and preparations of the state of the art.

Intermediates in the preparation of the active substances according to the invention can preferably be obtained in accordance with the following reaction scheme (reaction scheme I):

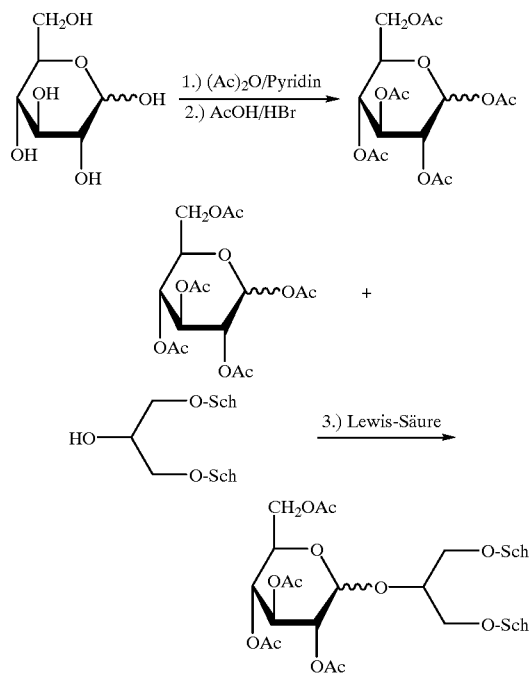

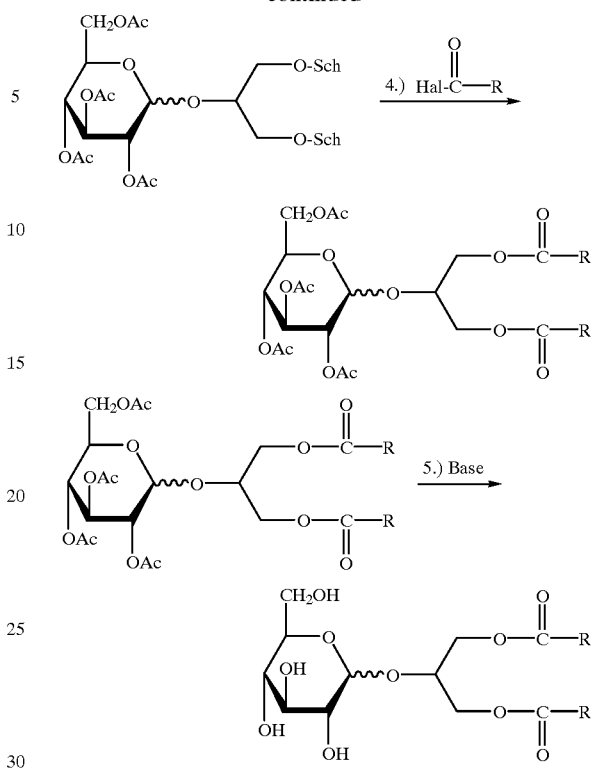

(Pyridin = pyridine; Lewis-Säure = Lewis acid)

The symbol "Ac" within a molecule represents "acetyl". The symbol "R" represents an alkyl radical on which the acyl radicals $R_1$ and $R_2$ are based.

Reaction steps 1.) and 2.) are often optional because a number of acetylated brominated sugars of the structure

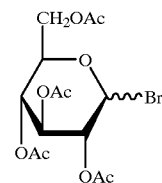

are known and are commercially available.

Reaction step 3.) is advantageously carried out choosing silver carbonate as the Lewis acid and choosing methylene chloride as the solvent for the sugar derivative. The symbol "Sch" represents "protecting group", it also being possible for the two protecting groups to be joined together so as to form a ring with the glyceryl radical, as exemplified by 5-hydroxy-2-phenyl-1,3-dioxane:

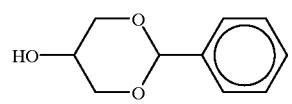

Reaction of the intermediate obtained in reaction step 3.) with an acyl halide (advantageously acyl chloride) in a subsequent reaction step 4.), in a basic medium, preferably with the addition of pyridine, and basic hydrolysis (for example by means of methylamine in methyl alcohol, but preferably selective hydrazinolytic deacetylation) in a subsequent reaction step 5.), leads to the glycoglycerolipids according to the invention.

Another advantageous reaction scheme in the preparation of the active substances according to the invention is shown below (reaction scheme II):

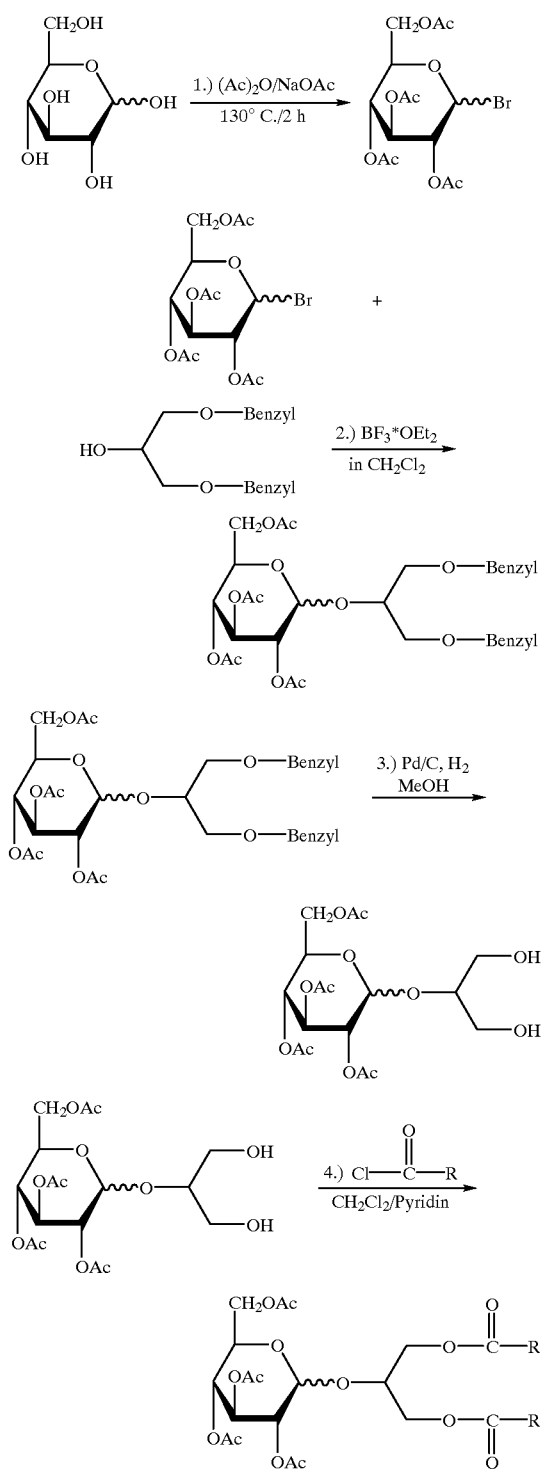

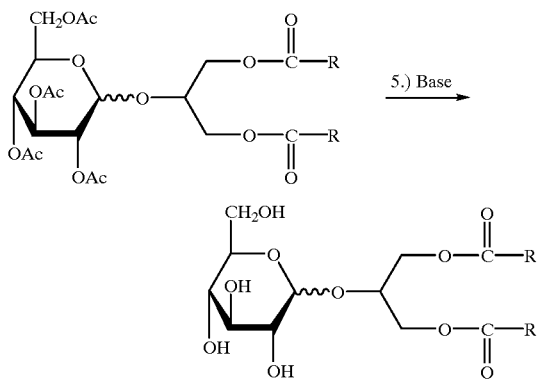

(Benzyl = benzyl; Pyridin = pyridine)

The base shown in reaction step 5.) is advantageously $N_2H_5OH$, especially in a mixture of 85% ethyl alcohol and chloroform (1:1), this reaction step preferably being carried out at ca. 85° C. over a period of ca. 1 hour.

Advantageous acetamidoglycoglycerides or aminoglycoglycerides are obtained by the following route (reaction scheme III):

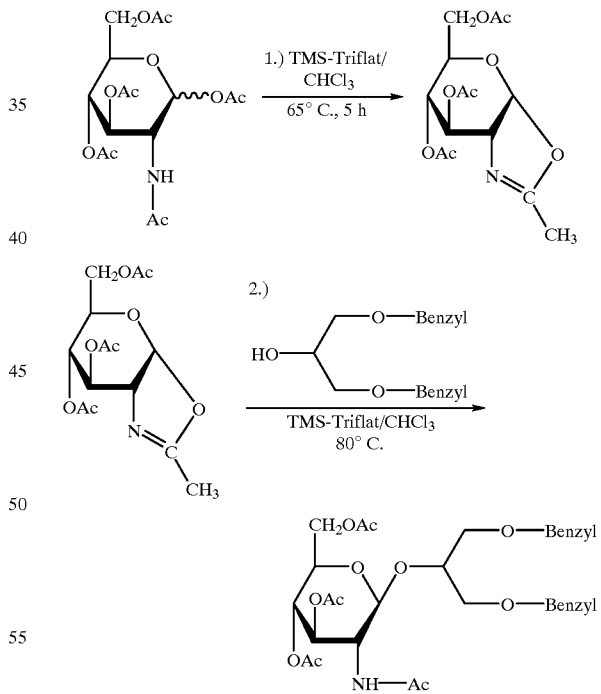

(TMS-Triflat = TMS triflate; Benzyl = benzyl)

Starting from the product obtained in reaction step 2.), one possibility is then to proceed analogously to reaction scheme II, affording products of the structural formula

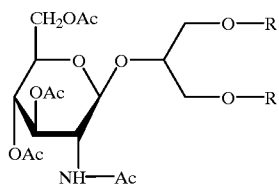

for example.

However, it is also possible and advantageous to convert the acetamido group to an amino group, for example by selective deacetylation, affording products of the structural formula

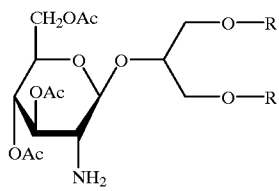

for example.

The active substances according to the invention are prepared by conventional methods familiar to those skilled in the art.

The cosmetic or dermatological formulations according to the invention can have the conventional compositions and can be used for the treatment, care and cleansing of the skin and/or hair and as cosmetic make-up products. They advantageously contain 0.001% by weight to 95% by weight, preferably 0.01% by weight to 25% by weight but especially 0.25% by weight to 5% by weight of the glycoglycerolipids according to the invention, based on the total weight of the preparations.

For use, the cosmetic and dermatological preparations according to the invention are applied to the skin and/or hair in sufficient amount and in the manner conventional for cosmetics.

Cosmetic and dermatological preparations according to the invention can have a variety of forms. Thus they can be in the form of e.g. a solution, an anhydrous preparation, an emulsion or microemulsion of the water-in-oil (W/O) type or oil-in-water (O/W) type, a multiple emulsion, for example of the water-in-oil-in-water (W/O/W type), a gel, an aqueous dispersion, a solid stick, an ointment or else an aerosol. It is also advantageous to present the glycoglycerolipids according to the invention in encapsulated form, e.g. encapsulated in collagen matrices and other conventional encapsulating materials, e.g. as cellulose encapsulations, or encapsulated in gelatin, wax matrices or liposomes.

It is also possible and advantageous, in terms of the present invention, to introduce the glycoglycerolipids according to the invention into aqueous systems or surfactant preparations for cleansing the skin and hair.

The cosmetic and dermatological preparations according to the invention can contain cosmetic auxiliaries such as those conventionally used in such preparations, e.g. preservatives, bactericides, perfumes, antifoams, dyes, pigments with a colouring effect, thickeners, surface-active substances, emulsifiers, plasticizing, moisturizing and/or moisture-retaining substances, fats, oils, waxes or other conventional constituents of a cosmetic or dermatological formulation, such as alcohols, polyols, polymers, foam stabilizers, electrolytes, organic solvents or silicone derivatives.

In particular, the glycoglycerolipids according to the invention can also be combined with antioxidants.

According to the invention, favourable antioxidants which can be used are any antioxidants suitable or conventional for cosmetic and/or dermatological applications.

The antioxidants are advantageously selected from the group comprising amino acids (e.g. glycine, histidine, tyrosine, tryptophan) and their derivatives, imidazoles (e.g. urocanic acid) and their derivatives, peptides such as D,L-carnosine, D-carnosine, L-carnosine and their derivatives (e.g. anserine), carotenoids, carotenes (e.g. α-carotene, β-carotene, lycopene) and their derivatives, chlorogenic acid and its derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl, lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very low tolerated doses (e.g. pmol to $\mu$mol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and its derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin, rutinic acid and its derivatives, α-glycosylrutin, ferulic acid, furfurylideneglucitol, carnosine, butylhydroxytoluene, butylhydroxyanisole, nordihydroguaiac acid, nordihydroguaiaretic acid, trihydroxybutyrophenone, uric acid and its derivatives, mannose and its derivatives, zinc and its derivatives (e.g. ZnO, ZnSO$_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active substances which are suitable according to the invention.

The amount of the abovementioned antioxidants (one or more compounds) in the preparations according to the invention is preferably 0.001 to 30% by weight, particularly preferably 0.05–20% by weight and especially 1–10% by weight, based on the total weight of the preparation.

If the antioxidant or antioxidants are vitamin E and/or its derivatives, their respective concentrations are advantageously chosen within the range 0.001–10% by weight, based on the total weight of the formulation.

If the antioxidant or antioxidants are vitamin A or vitamin A derivatives or carotenes or their derivatives, their respective concentrations are advantageously chosen within the range 0.001–10% by weight, based on the total weight of the formulation.

Emulsions according to the invention are advantageous and contain e.g. said fats, oils, waxes and other fatty substances, as well as water and an emulsifier such as that conventionally used for this type of formulation.

The lipid phase can advantageously be selected from the following group of substances:

natural, synthetic and/or partially synthetic oils such as the triglycerides of capric or caprylic acid, but preferably castor oil;

fats, waxes and other natural, synthetic and/or partially synthetic fatty substances, preferably esters of fatty acids with alcohols having a small number of C atoms, e.g. with isopropanol, propylene glycol or glycerol, or esters of fatty alcohols with alkanoic acids having a small number of C atoms or with fatty acids;

silicone oils such as dimethylpolysiloxanes, diethylpolysiloxanes, diphenylpolysiloxanes and mixed forms thereof;

saturated compounds such as hydrocarbons of natural or synthetic origin (Vaseline, squalane).

The aqueous phase of the preparations according to the invention may advantageously contain alcohols, diols or polyols with a small number of C atoms, and their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and especially one or more thickeners which can advantageously be selected from the group comprising silicon dioxide, aluminium silicates and polysaccharides or their derivatives, e.g. hyaluronic acid, xanthan gum and hydroxypropyl methyl cellulose, and particularly advantageously from the group comprising polyacrylates, preferably a polyacrylate from the group comprising the so-called Carbopols, for example Carbopols of types 980, 981, 1382, 2984 and 5984, in each case individually or in combination.

In particular, mixtures of the abovementioned solvents are used. Water can be a further constituent of alcoholic solvents.

Emulsions according to the invention are advantageous and contain e.g. said fats, oils, waxes and other fatty substances, as well as water and an emulsifier such as that conventionally used for this type of formulation.

Gels according to the invention conventionally contain alcohols with a small number of C atoms, e.g. ethanol, isopropanol, propane-1,2-diol or glycerol, and water or one of the abovementioned oils in the presence of a thickener, said thickener being preferably silicon dioxide or an aluminium silicate in the case of oily-alcoholic gels or preferably a polyacrylate in the case of aqueous-alcoholic or alcoholic gels.

Suitable propellants for preparations according to the invention which can be sprayed from aerosol containers are the conventional known liquefied propellants of high volatility, for example hydrocarbons (propane, butane, isobutane), which can be used on their own or in a mixture with one another. Compressed air can also advantageously be used.

Preparations according to the invention can also advantageously contain substances which absorb UV radiation in the UVB region, the total amount of filters being e.g. 0.1% by weight to 30% by weight, preferably 0.5 to 10% by weight and especially 1.0 to 6.0% by weight, based on the total weight of the preparations, in order to provide cosmetic preparations which protect the hair or skin from the whole range of ultraviolet radiation. They can also be used as sunscreens for the hair or skin.

If the emulsions according to the invention contain UVB filters, these can be oil-soluble or water-soluble. Examples of oil-soluble UVB filters which are advantageous according to the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino) benzoate;

cinnamic acid esters, preferably 2-ethylhexyl 4-methoxycinnamate, isopentyl 4-methoxycinnamate;

salicylic acid esters, preferably 2-ethylhexyl salicylate, 4-isopropylbenzyl salicylate, homomenthyl salicylate;

benzophenone derivatives, preferably 2-hydroxy-4-methoxybenzophenone, 2-hydroxy-4-methoxy-4'-methylbenzophenone, 2,2'-dihydroxy-4-methoxybenzophenone;

benzalmalonic acid esters, preferably di(2-ethylhexyl) 4-methoxybenzalmalonate;

2,4,6-trianilino(p-carbo-2'-ethyl-1'-hexyloxy)-1,3,5-triazine.

Examples of advantageous water-soluble UVB filters are:

2-phenylbenzimidazole-5-sulphonic acid salts such as its sodium or potassium salt or its triethanolammonium salt, as well as the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, e.g. 4-(2-oxo-3-bornylidenemethyl)benzenesulphonic acid, 2-methyl-5-(2-oxo-3-bornylidenemethyl) benzenesulphonic acid and their salts.

Of course, the list of said UVB filters which can be used in combination with the glycoglycerolipids according to the invention is not intended to imply a limitation.

It can also be advantageous to combine glycoglycerolipids according to the invention with UVA filters which have hitherto conventionally been present in cosmetic preparations. These substances are preferably dibenzoylmethane derivatives, especially 1-(4'-tert-butylphenyl)-3-(4'-methoxyphenyl)propane-1,3-dione and 1-phenyl-3-(4'-isopropylphenyl)propane-1,3-dione. The invention also provides these combinations or preparations containing these combinations. The amounts can be those used for the UVB combination.

The invention also provides the use of a combination of the glycoglycerolipids according to the invention with at least one UVA filter as antioxidant, or to the use of a combination of the glycoglycerolipids according to the invention with at least one UVA filter as antioxidant in a cosmetic or dermatological preparation.

The invention also provides the use of a combination of the glycoglycerolipids according to the invention with at least one UVA filter and at least one UVB filter as antioxidant, or the use of a combination of the glycoglycerolipids according to the invention with at least one UVA filter and at least one UVB filter as antioxidant in a cosmetic or dermatological preparation.

Cosmetic and dermatological preparations with an effective content of glycoglycerolipids according to the invention can also contain inorganic pigments which are conventionally used in cosmetics for protecting the skin from UV rays. Said inorganic pigments are oxides of titanium, zinc, iron, zirconium, silicon, manganese, aluminium and cerium and mixtures thereof, as well as modifications in which the oxides are the active agents. Pigments based on titanium dioxide are particularly preferred.

The invention also provides these combinations of UVA filter and pigment or preparations containing these combinations. The amounts used can be those mentioned for the above combinations.

Examples of cosmetic and dermatological preparations for protecting the hair from UV rays according to the invention are shampoos, preparations used when rinsing the hair before or after shampooing, before or after perming or before or after dyeing or bleaching, hair drying or setting preparations, dyeing or bleaching preparations, a hair conditioning lotion, a hair lacquer or perming compositions.

The cosmetic and dermatological preparations contain active substances and auxiliaries such as those conventionally used for hair care and conditioning preparations of this type. Auxiliaries used are preservatives, surface-active substances, antifoams, thickeners, emulsifiers, fats, oils, waxes, organic solvents, bactericides, perfumes, dyes or pigments whose purpose is to colour the hair or the cosmetic or dermatological preparation itself, electrolytes and substances for combating greasy hair.

Electrolytes in terms of the present invention are understood as meaning water-soluble alkali metal, ammonium, alkaline earth metal (including magnesium) and zinc salts of inorganic anions and any mixtures of such salts, it being essential to ensure that these salts are pharmaceutically or cosmetically acceptable.

The anions according to the invention are preferably selected from the group comprising chlorides, sulphates and hydrogensulphates, phosphates, hydrogenphosphates and linear and cyclic oligophosphates, and carbonates and hydrogencarbonates.

Cosmetic preparations which are in the form of a skin cleanser or shampoo preferably contain at least one additional anionic, non-ionic or amphoteric surface-active substance or mixtures of such substances, glycoglycerolipids according to the invention in the aqueous medium, and auxiliaries such as those conventionally used for this purpose. The additional surface-active substance or the mixtures of these substances can be present in the shampoo in a concentration of between 1% by weight and 50% by weight.

If the cosmetic or dermatological preparations are in the form of a lotion which is used e.g. before or after dyeing, before or after shampooing, between two shampoo applications or before or after perming, and rinsed out, said preparations are e.g. aqueous or aqueous-alcoholic solutions which may contain additional surface-active substances, the concentration of which can be between 0.1 and 10% by weight, preferably between 0.2 and 5% weight.

These cosmetic or dermatological preparations can also take the form of aerosols with the auxiliaries conventionally used for this purpose.

A cosmetic preparation in the form of a non-rinse lotion, especially a hair setting lotion, a hair drying lotion or a hair conditioning lotion, is generally an aqueous, alcoholic or aqueous-alcoholic solution and contains at least one cationic, anionic, non-ionic or amphoteric polymer or mixtures thereof, as well as active substance combinations according to the invention in an effective concentration. The amount of polymers used is e.g. between 0.1 and 10% by weight, preferably between 0.1 and 3% by weight.

Cosmetic hair conditioning and hair care preparations containing glycosylglycerides according to the invention can take the form of emulsions of the non-ionic or anionic type. As well as water, non-ionic emulsions contain oils or fatty alcohols which can also be polyethoxylated or polypropoxylated, for example, or else mixtures of both organic components. These emulsions may contain cationic surface-active substances.

According to the invention, cosmetic hair conditioning and hair care preparations can take the form of gels which, in addition to having an active content of glycoglycerolipids according to the invention and solvents conventionally used for this purpose, preferably water, also contain organic thickeners, e.g. gum arabic, xanthan gum, sodium alginate or cellulose derivatives, preferably methyl cellulose, hydroxymethyl cellulose, hydroxyethyl cellulose, hydroxypropyl cellulose or hydroxypropyl methyl cellulose, or inorganic thickeners, e.g. aluminium silicates such as bentonites, or a mixture of polyethylene glycol and polyethylene glycol stearate or distearate. The thickener is present in the gel in an amount e.g. of between 0.1 and 30% by weight, preferably of between 0.5 and 15% by weight.

The amount of glycoglycerolipids according to the invention in a composition intended for the hair is preferably 0.05% by weight to 10% by weight, especially 0.5% by weight to 5% by weight, based on the total weight of the composition.

Aqueous cosmetic cleansers according to the invention or low-water or water-free cleanser concentrates intended for aqueous cleansing can contain anionic, non-ionic and/or amphoteric surfactants, for example conventional soaps, e.g. fatty acid salts of sodium, alkylsulphates, alkyl ether sulphates, alkanesulphonates, alkylbenzenesulphonates, sulphoacetates, sulphobetaines, sarcosinates, amidosulphobetaines, sulphosuccinates, sulphosuccinic acid half-esters, alkyl ether carboxylates, protein/fatty acid condensates, alkylbetaines and amidobetaines, fatty acid alkanolamides and/or polyglycol ether derivatives.

Cosmetic preparations which are in the form of cosmetic skin cleansing preparations can be liquid or solid. In addition to glycoglycerolipids according to the invention, they preferably contain at least one anionic, non-ionic or amphoteric surface-active substance or mixtures thereof, one or more electrolytes if desired, and auxiliaries such as those conventionally used for this purpose. The surface-active substance can be present in the cleansing preparations in a concentration of between 1 and 94% by weight, based on the total weight of the preparations.

In addition to having an effective content of glycoglycerolipids according to the invention, cosmetic preparations in the form of a shampoo preferably contain at least one anionic, non-ionic or amphoteric surface-active substance or mixtures thereof, optionally an electrolyte according to the invention and auxiliaries such as those conventionally used for this purpose. The surface-active substance can be present in the shampoo in a concentration of between 1% by weight and 94% by weight.

Apart from the abovementioned surfactants, the compositions according to the invention contain water and optionally the additives conventionally used in cosmetics, for example perfume, thickeners, dyes, deodorants, antimicrobial substances, superfatting agents, complexing agents and sequestering agents, pearlescent agents, plant extracts, vitamins, active substances and the like.

The invention also provides the process for the preparation of the cosmetic compositions according to the invention, which is characterized in that glycoglycerolipids according to the invention are incorporated into cosmetic and dermatological formulations in a manner known per se.

The following Examples will illustrate the present invention without implying a limitation.

EXAMPLE 1

(O/W Emulsion)

|  | % by weight |
| --- | --- |
| Glycerol monostearate | 2.00 |
| 1,3-Di-O-hexadecyl-2-O-(D-glucopyranosyl)-sn-glycerol | 2.00 |
| Paraffin oil, subliquidum | 11.00 |
| Octyldodecanol | 4.00 |
| Hydrogenated coconut fatty acid glycerides | 1.00 |
| Cyclomethicone | 1.00 |
| Carbomer | 0.15 |
| Glycerol | 2.00 |
| Tocopheryl acetate | 0.50 |
| Perfume, preservative, NaOH, dyes, antioxidants etc. | q.s. |
| Water | ad 100.00 |

EXAMPLE 2

(O/W Emulsion)

|  | % by weight |
| --- | --- |
| Stearic acid | 1.50 |
| Sorbitan monostearate | 0.50 |
| 1,3-Di-O-hexadecyl-2-O-(D-glucopyranosyl)-sn-glycerol | 2.00 |
| Myristyl alcohol | 1.50 |
| Glycerol monostearate | 0.50 |
| Paraffin oil, subliquidum | 10.00 |
| Dimethicone | 1.00 |
| Octyldodecanol | 2.00 |
| Hydrogenated coconut fatty acid glycerides | 0.50 |
| Carbomer | 0.10 |
| Serine | 0.50 |
| Glycerol | 2.00 |
| Tocopheryl acetate | 0.50 |
| Dyes, antioxidants etc. | q.s. |
| Water | ad 100.00 |

EXAMPLE 3

(O/W Emulsion)

|  | % by weight |
| --- | --- |
| Sorbitan monostearate | 2.00 |
| Laurylmethicone copolyol | 0.35 |
| Cetylmethicone copolyol | 0.15 |
| 1,3-Di-O-hexadecyl-2-O-(D-glucopyranosyl)-sn-glycerol | 2.00 |
| Paraffin oil, subliquidum | 10.00 |
| Octyldodecanol | 4.00 |
| Hydrogenated coconut fatty acid glycerides | 1.00 |
| Cyclomethicone | 1.00 |
| Dimethicone | 1.00 |
| Carbomer | 0.15 |
| Glycerol | 2.00 |
| Tocopheryl acetate | 0.50 |
| Dyes, antioxidants etc. | q.s. |
| Water | ad 100.00 |

EXAMPLE 4

(Shampoo)

|  | % by weight |
| --- | --- |
| Sodium lauryl ether sulphate (27.5%) | 25.00 |
| 1,3-Di-O-dodecyl-2-O-(D-glucopyranosyl)-sn-glycerol | 4.00 |
| Dyes, preservative, pearlescent agent | q.s. |
| Water | ad 100.00 |

EXAMPLE 5

(Shampoo)

|  | % by weight |
| --- | --- |
| Alkyl polyglucose (50%) | 16.00 |
| 1,3-Di-O-dodecyl-2-O-(D-glucopyranosyl)-sn-glycerol | 4.00 |
| Dyes, preservative, pearlescent agent | q.s. |
| Water | ad 100.00 |

EXAMPLE 6

(Shampoo)

|  | % by weight |
| --- | --- |
| Sodium lauryl ether sulphate (27.5%) | 14.00 |
| Alkyl polyglucose (50%) | 8.00 |
| 1,3-Di-O-dodecyl-2-O-(D-glucopyranosyl)-sn-glycerol | 4.00 |
| Dyes, preservative, pearlescent agent | q.s. |
| Water | ad 100.00 |

We claim:

1. Cosmetic or pharmaceutical preparations, comprising an effective content of one or more pharmaceutically and/or cosmetically acceptable glycoglycerolipid or glycoglycerolipids of the structures

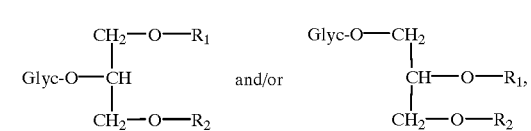

in which Glyc is a hexosyl or pentosyl residue or a dexoy sugar residue or an N-acetylglucosamine residue or a glucosamine residue coupled to the glyceryl radical via an α- or β-glycosidic linkage, in which $R_1$ and $R_2$ independently of one another represent H or saturated or unsaturated, branched or unbranched acyl having 1–24 carbon atoms, wherein at least one of the radicals $R_1$ and $R_2$ is an acyl radical.

2. Cosmetic or pharmaceutical preparations according to claim 1, wherein Glyc is a hexosyl residue in either a furanosyl form or a pyranosyl form.

3. Cosmetic or pharmaceutical preparations according to claim 1, wherein Glyc is a hexosyl residue and the hexoses on which the hexosylglycerolipids are based are at least one of aldohexoses or amino sugars.

4. Cosmetic or pharmaceutical preparations according to claim 3, wherein the aldohexoses are in their pyranoid form.

5. Cosmetic or pharmaceutical preparations according to claim 3, wherein the aldohexoses are at least one of allo(pyrano)se, altro(pyrano)se, gluco(pyrano)se, manno(pyrano)se, gulo(pyrano)se, ido(pyrano)se, galacto(pyrano)se or talo(pyrano)se.

6. Cosmetic or pharmaceutical preparations according to claim 3, wherein the hexosylglycerolipids are based on D- or L-ketohexoses.

7. Cosmetic or pharmaceutical preparations according to claim 6, wherein the D- or L-ketohexoses are at least one of psicose, fructose, sorbose, or togatose.

8. Cosmetic or pharmaceutical preparations according to claim 6, wherein the D- or L-ketohexoses are in the furanoid form.

9. Cosmetic or pharmaceutical preparations according to claim 1, wherein $R_1$ or $R_2$ are octanoyl, decanoyl, dodecanoyl, tetradecanoyl, hexadecanoyl, octadecanoyl and eicosanoyl.

10. Cosmetic or pharmaceutical preparations according to claim 3, wherein the hexosylglyerides upon which the hexosylglyerolipids are based are at least one of 1-monoacyl or 1-3 diacyl derivatives of 2-O-(β-D-glucopyranosyl)-sn-glycerol.

11. Cosmetic or pharmaceutical preparations according to claim 1, wherein the glycoglycerolipid or glycoglycerolipids are of the structure

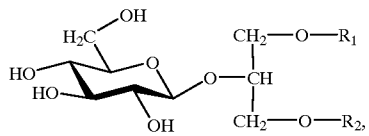

in which $R_1$ and $R_2$ independently of one another represent H or saturated or unsaturated, branched or unbranched acyl having 1–24 carbon atoms.

12. Cosmetic or pharmaceutical preparations according to claim 1, which contain 0.01% by weight to 25% by weight glycoglycerolipids, based on the total weight of the preparations.

13. Cosmetic or pharmaceutical preparations according to claim 1, which contain 0.25% by weight to 5% by weight glycoglycerolipids, based on the total weight of the preparations.

14. Cosmetic or pharmaceutical preparations according to claim 1, which further include from 0.001%–30% by weight of an antioxidant.

15. Cosmetic or pharmaceutical preparations according to claim 1, which further include from 0.1%–30% by weight of an ultraviolet filter.

16. In a method comprising applying to skin a cosmetic or pharmaceutical composition comprising a compound functioning as an agent for increasing the moisture content of the skin, as a surface-active substance, as a washing-active substance or as an emulsifier, wherein the improvement comprises using as said compound a glycoglycerolipid of the formula:

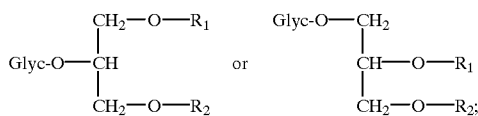

wherein Glyc is a hexosyl or pentosyl residue or a deoxy sugar residue or an N-acetylglucosamine residue or a glucosamine residue coupled to the glyceryl radical via an α- or β-glycosidic linkage, and $R_1$ and $R_2$ independently of one another represent H or saturated or unsaturated, branched or unbranched acyl having 1 to 24 carbon atoms, wherein at least one of the radicals $R_1$ and $R_2$ is an acyl radical.

* * * * *